United States Patent
Bergman

(10) Patent No.: US 10,533,891 B2
(45) Date of Patent: *Jan. 14, 2020

(54) INSPECTION SYSTEM FOR TURBINE ROTORS

(71) Applicant: General Electric Company, Schenectady, NY (US)

(72) Inventor: Robert William Bergman, Scotia, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,326

(22) Filed: Jun. 25, 2018

(65) Prior Publication Data

US 2018/0306636 A1   Oct. 25, 2018

Related U.S. Application Data

(63) Continuation of application No. 15/828,960, filed on Dec. 1, 2017, now Pat. No. 10,036,665, which is a
(Continued)

(51) Int. Cl.
*G01N 29/22* (2006.01)
*G01N 29/265* (2006.01)
*G01H 1/00* (2006.01)

(52) U.S. Cl.
CPC .......... *G01H 1/006* (2013.01); *G01N 29/225* (2013.01); *G01N 29/265* (2013.01)

(58) Field of Classification Search
CPC ..... G01H 1/006; G01N 29/265; G01N 29/225
(Continued)

(56) References Cited

U.S. PATENT DOCUMENTS 6,347,550 B1   2/2002  Kroening et al.
7,190,162 B2 *  3/2007  Tenley ............... G01N 27/9013
                                                    324/238
(Continued)

FOREIGN PATENT DOCUMENTS

DE   10 2011 050051 A1   11/2012

OTHER PUBLICATIONS

Gunarathne, G.P.P., and Quereshi, Y., "A Novel Technique for dynamic alignment of ultrasonic transducers in real-time non-destructive testing," In Proceedings of the Instrumentation and Measurement Technology Conference, vol. 2, pp. 1137-1142 (May 20-22, 2003) (Abstract).
(Continued)

*Primary Examiner* — Jacques M Saint Surin
(74) *Attorney, Agent, or Firm* — Perttu Juhana Henttonen; Hoffman Warnick LLC

(57) ABSTRACT

An inspection system includes a first ultrasonic probe positioned on and configured to move along a surface of a component. The first ultrasonic probe transmits ultrasonic energy. The inspection system also includes a second ultrasonic probe positioned on and configured to move along the surface of the component opposite the first probe. The second ultrasonic probe receives the ultrasonic energy transmitted by the first ultrasonic probe. Additionally, the inspection system includes a probe alignment system in communication with the first ultrasonic probe and the second ultrasonic probe. The probe alignment system is configured to analyze an energy characteristic for the ultrasonic energy received by the second ultrasonic probe to determine if a displacement characteristic for at least one of the first ultrasonic probe and the second ultrasonic probe requires adjustment.

13 Claims, 5 Drawing Sheets

Related U.S. Application Data continuation of application No. 15/200,082, filed on Jul. 1, 2016, now Pat. No. 10,151,625.

(58) Field of Classification Search
USPC .......................................................... 73/660
See application file for complete search history.

(56) References Cited

U.S. PATENT DOCUMENTS

| | | | |
|---|---|---|---|
| 7,228,741 | B2 | 6/2007 | Georgeson et al. |
| 9,791,421 | B2 | 10/2017 | Fassi |
| 10,036,665 | B2 | 7/2018 | Bergman |
| 2005/0223809 | A1 | 10/2005 | Murphy et al. |
| 2006/0053891 | A1 | 3/2006 | Georgeson et al. |
| 2007/0017297 | A1 | 1/2007 | Georgeson et al. |
| 2008/0079426 | A1* | 4/2008 | Suzuki ............... G01N 27/902 324/238 |
| 2008/0218181 | A1 | 9/2008 | Ducheminsky et al. |
| 2012/0024067 | A1 | 2/2012 | Oberdoerfer et al. |
| 2012/0055255 | A1 | 3/2012 | Metala et al. |
| 2012/0140865 | A1 | 6/2012 | Vigliano |
| 2013/0291640 | A1 | 11/2013 | Rasselkorde et al. |
| 2014/0312739 | A1 | 10/2014 | Bar-Cohen et al. |
| 2016/0038118 | A1 | 2/2016 | Chaggares et al. |
| 2018/0003549 | A1 | 1/2018 | Bergman |

OTHER PUBLICATIONS

International Search Report and Written Opinion issued in connection with corresponding PCT Application No. PCT/US2017/40518, dated Sep. 28, 2017.

U.S. Appl. No. 15/828,960, Notice of Allowance dated Apr. 27, 2018, 17 pages.

U.S. Appl. No. 15/200,082, Notice of Allowance dated Sep. 10, 2018, 9 pages.

\* cited by examiner

INSPECTION SYSTEM FOR TURBINE ROTORS

TECHNICAL FIELD

The disclosure relates generally to an inspection system, and more particularly, to inspection probes of an inspection system and a process of maintaining a desired alignment between the inspection probes of the inspection system.

BACKGROUND

Over the operational life of a turbine system, components of the system require regular inspection and/or maintenance. The inspection processes performed on the turbine system may ensure that the components are not damaged, obstructed, properly aligned/positioned, and/or functioning at a desired efficiency level so the turbine system may generate the greatest amount of energy without damaging the system. When the inspection process determines that there is an operational and/or functional issue with a component of the turbine system (e.g., damaged, misaligned and so on), maintenance (e.g., repair, replacement and the like) may be performed on the component and/or system before the turbine system become operational again.

Adequate inspection of the components of the turbine system may be difficult however because of the configuration of the system. For example, a rotor of the turbine system may be encased and/or enclosed within a housing and may include and/or be surrounded by a plurality of features (e.g., turbine buckets, stators and so on) crucial to the operation of the turbine system. As a result, the clearance and accessibility of the rotor of the turbine system may be limited; making inspection of the rotor difficult. In conventional processes, the rotor may be visually inspected by an operator by removing some components on and/or surrounding the rotor. However, the quality of the visual inspection may vary and may depend on the operator conducting the inspection.

In other conventional processes, the rotor may be removed from the housing, and conventional inspection devices, such as sensors, may be used when performing the inspection process. However, the conventional inspection devices may have a difficult time accurately inspecting the rotor because of the number of unique geometries and/or features included on the rotor. Specifically, the non-uniform geometries and/or features included on the rotor of the turbine system may obstruct and/or block lines of sight between the conventional inspection devices used to inspect the rotor. Where the line of sight is obstructed, the results of the inspection generated by the conventional inspection device may be skewed and/or incomplete because the conventional inspection devices have trouble accurately inspecting areas of the rotor that include these unique geometries and/or features.

SUMMARY

A first aspect of the disclosure provides an inspection system. The inspection system may include a first ultrasonic probe positioned on and configured to move along a surface of a component. The first ultrasonic probe may be configured to transmit ultrasonic energy. The inspection system may also include a second ultrasonic probe positioned on and configured to move along the surface of the component opposite the first probe. The second ultrasonic probe may be configured to receive the ultrasonic energy transmitted by the first ultrasonic probe. Additionally, the inspection system may include a probe alignment system in communication with the first ultrasonic probe and the second ultrasonic probe. The probe alignment system may be configured to analyze an energy characteristic for the ultrasonic energy received by the second ultrasonic probe to determine if a displacement characteristic for at least one of the first ultrasonic probe and the second ultrasonic probe requires adjustment.

A second aspect of the disclosure provides a rotor. The rotor may include a plurality of features formed on and extending from an exposed surface, and an inspection system. The inspection system may include at least one transmitter probe positioned on the exposed surface and adjacent the plurality of features. The at least one transmitter probe may be configured to transmit energy. The inspection system may also include at least one receiver probe positioned on the exposed surface and separated from the at least one transmitter probe by the plurality of features. The at least one receiver probe may be configured to receive the energy transmitted by the at least one transmitter probe. Additionally, the inspection system may include a probe alignment system in communication with the at least one transmitter probe and the at least one receiver probe. The probe alignment system may be configured to analyze an energy characteristic for the ultrasonic energy received by the at least one receiver probe to determine if a displacement characteristic for at least one of the at least one transmitter probe and the at least one receiver probe requires adjustment.

A third aspect of the disclosure provides a method for aligning inspection probes. The method may include moving a first ultrasonic probe along a surface of a component. The first ultrasonic probe may be configured to transmit energy. The method may also include moving a second ultrasonic probe along the surface of the component, where the second ultrasonic probe may be configured to receive the energy transmitted by the first ultrasonic probe. Additionally, the method may also include analyzing an energy characteristic for the energy received by the second ultrasonic probe, and adjusting a displacement characteristic for at least one of the first ultrasonic probe and the second ultrasonic probe based on the analyzed energy characteristic.

A fourth aspect of the disclosure provides an inspection system for inspecting a turbine rotor. The inspection system may include a first probe for positioning on a circumferential surface of the turbine rotor; a first inclinometer for positioning at one of: on the first probe or adjacent the first probe; a second probe for positioning on the circumferential surface of the turbine rotor, axially adjacent the first probe; a second inclinometer for positioning at one of: on the second probe or adjacent the second probe; and a probe alignment system in communication with the first inclinometer and the second inclinometer, the probe alignment system configured to axially align the first probe and second probe on the turbine rotor by: adjusting at least one of a first circumferential position of the first probe or a second circumferential position of the second probe in response to determining the first circumferential position of the first probe detected by the first inclinometer is distinct from the second circumferential position of the second probe detected by the second inclinometer.

BRIEF DESCRIPTION OF THE DRAWINGS

The disclosure will be readily understood by the following detailed description in conjunction with the accompanying drawings, wherein like reference numerals designate like structural elements, and in which.

Figure 1:
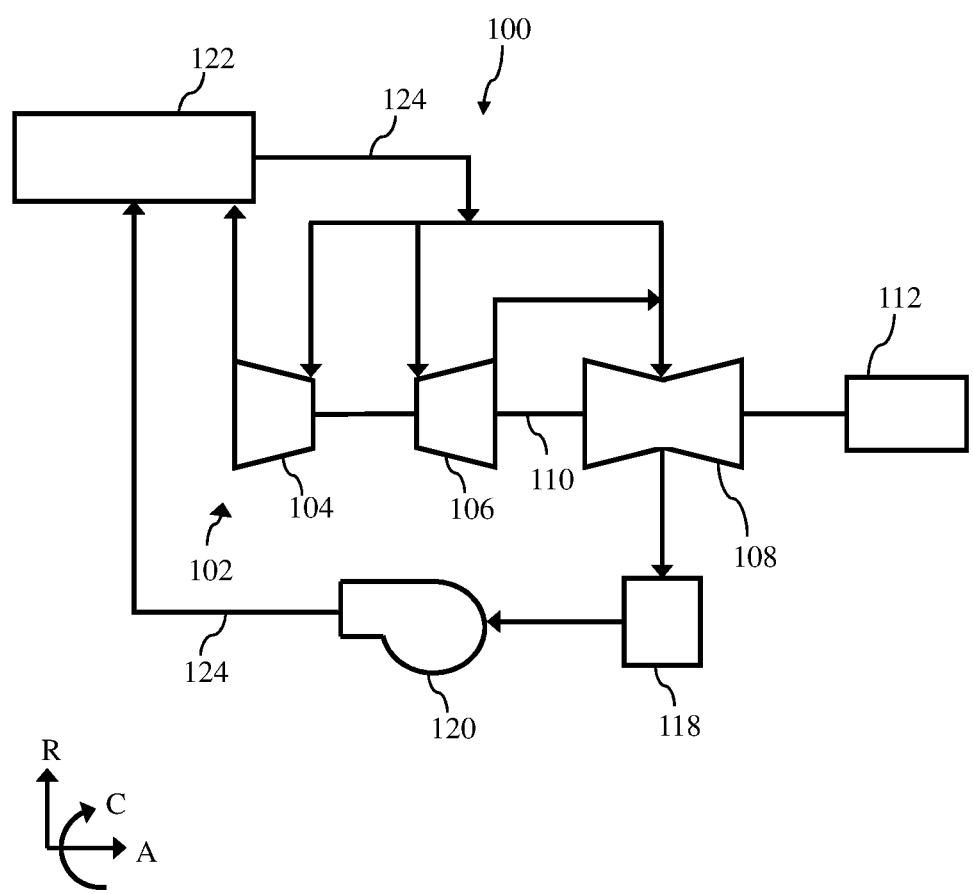
FIG. 1 shows a schematic view of a steam turbine system according to embodiments.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates generally to an inspection system, and more particularly, to inspection probes of an inspection system and a process of maintaining a desired alignment between the inspection probes of the inspection system.

These and other embodiments are discussed below with reference to FIGS. 1-5. However, those skilled in the art will readily appreciate that the detailed description given herein with respect to these Figures is for explanatory purposes only and should not be construed as limiting.

Turning to FIG. 1, a schematic depiction of a steam turbine system 100 is shown according to embodiments of the disclosure. Steam turbine system 10, as shown in FIG. 1 may be a conventional steam turbine system. As such, a brief description of the steam turbine system 100 is provided for clarity. As shown in FIG. 1, steam turbine system 100 may include a steam turbine component 102, including a high-pressure section 104, an intermediate-pressure section 106 and a low-pressure section 108, coupled to a rotor 110 of steam turbine system 10. Rotor 110 may also be coupled to a generator 112 for creating electricity during operation of steam turbine system 10. As shown in FIG. 1, steam turbine system 100 may also include a condenser 118 in fluid communication with low-pressure section 108 of steam turbine component 102, a pump 120 in fluid communication with condenser 118 and a heat recovery steam generation (HRSG) 122 in fluid communication with the pump and steam turbine component 102. The components (e.g., condenser 118, pump 120, HRSG 122) of steam turbine system 100 may be in fluid communication with one another via steam conduits 124.

During operation of steam turbine system 10, as shown in FIG. 1, steam is generated by HRSG 122 and provided to steam turbine component 102. More specifically, HRSG 122, amongst other steam sources (not shown), may provide steam to high-pressure section 104, intermediate-pressure section 106 and low-pressure section 108 via conduits 124 to flow through steam turbine component 102. Each section (e.g., low-pressure section 108) of steam turbine component 102 may include a plurality of turbine airfoils including a plurality of stages of buckets positioned in series on rotor 110, and a plurality of stator nozzles positioned adjacent the plurality of buckets. As steam flows over each stage of buckets, rotor 110 may be rotated and generator 112 may create power (e.g., electric current). The plurality of corresponding stator nozzles may aid in directing the steam toward the plurality of stages of buckets during operation of steam turbine system 10. The steam may exit steam turbine component 102, specifically low-pressure section 108, and may be condensed by condenser 118 and provided to HRSG 122 via pump 120. The condensed-steam may then aid in the generation of more steam by HRSG 122 and may adjacently be provided to steam turbine component 102.

As used herein, the terms "axial" and/or "axially" refer to the relative position/direction of objects along axis (A), which is substantially parallel with the axis of rotation of steam turbine system 100 (in particular, the rotor section). As further used herein, the terms "radial" and/or "radially" refer to the relative position/direction of objects along axis (R), which is substantially perpendicular with axis (A) and intersects axis (A) at only one location. Additionally, the terms "circumferential" and/or "circumferentially" refer to the relative position/direction (C) of objects along a circumference which surrounds axis (A) but does not intersect the axis (A) at any location.

Figure 2:
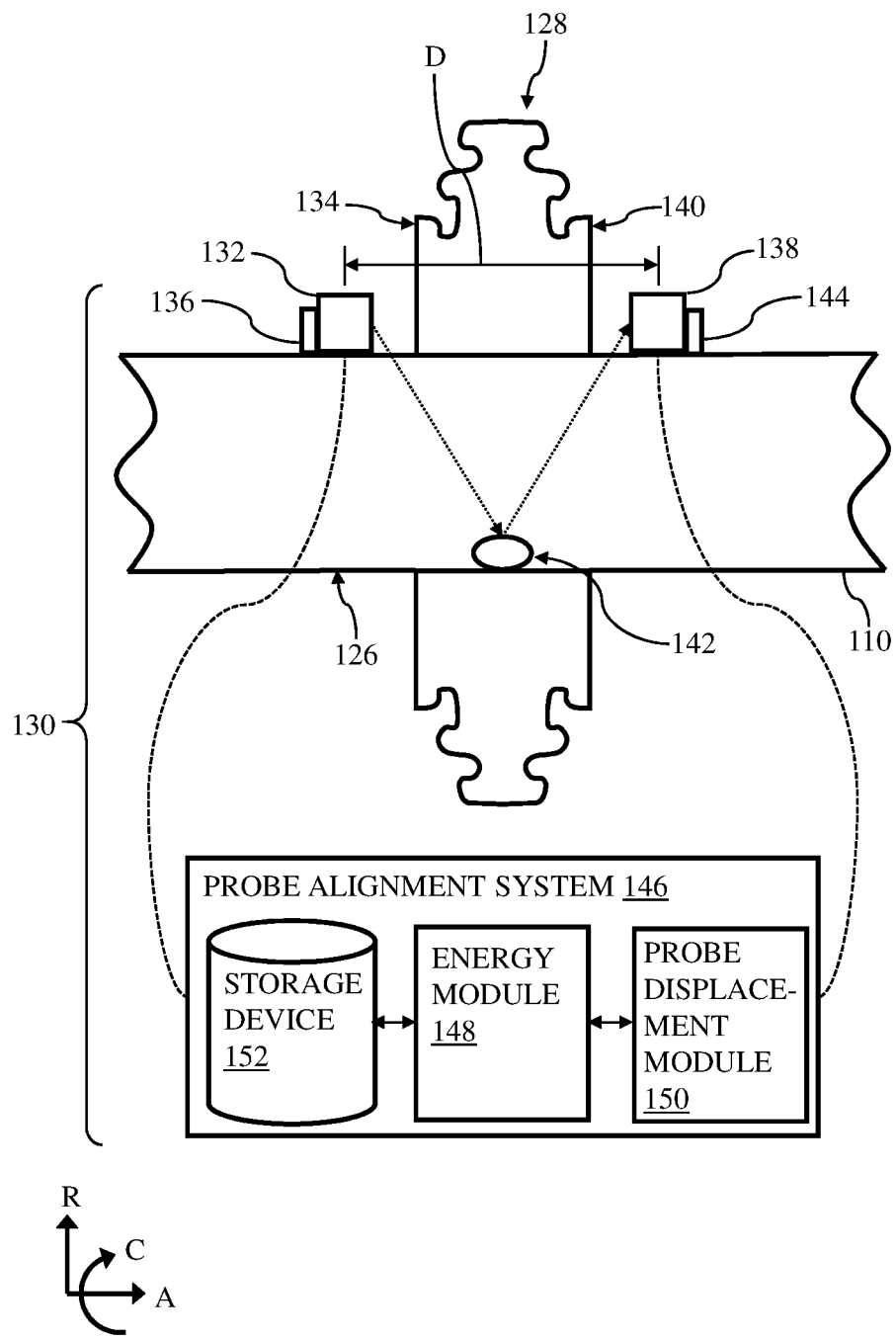
FIG. 2 depicts a side view of a portion of a rotor of the steam turbine system of FIG. 1, and an inspection system, according to embodiments.

FIG. 2 depicts a side view of a portion of rotor 110 of steam turbine system 100, according to embodiments. The portion of rotor 110 depicted in FIG. 2 may be a portion of rotor 110 positioned within a section (e.g., low-pressure section 108) of steam turbine component 102. In a non-limiting example, rotor 110 may be completely removed from an enclosure of the section of steam turbine component 102 that may house and/or surround the portion of rotor 110 when performing the inspection process discussed herein. Where rotor 110 is completely removed from the enclosure, rotor 110 may undergo a surface cleaning and/or roughening process (e.g., sandblasting) prior to performing the inspection process. In other non-limiting examples, rotor 110 may remain in a portion (e.g., half-shell) of the enclosure during the inspection process, or alternatively, rotor 110 may remain in the entire enclosure of the section of steam turbine component 102 where portions of rotor 110 may be accessible to the components configured to perform the inspection process.

Rotor 110 may include an exposed surface 126 and a plurality of features 128 formed on exposed surface 126. More specifically, the plurality of features 128 of rotor 110 may be formed on, extend from and/or project radially from exposed surface 126 of rotor 110. The plurality of features 128 of rotor 110 may also be positioned and/or formed on exposed surface 126 substantially around the circumference of rotor 110. In a non-limiting example shown in FIG. 2, the plurality of features 128 may include dovetails formed on and circumferentially around rotor 110. The dovetails may couple the turbine buckets (not shown) of steam turbine system 100 to rotor 110. Although only a single row of the plurality of features 128 are shown, it is understood that rotor 110 of steam turbine system 100 may include multiple rows of the plurality of features 128 formed on and separated axially along the length of rotor 110. Additionally, it is understood that the plurality of features 128 of rotor 110 may include various parts, segments, transitions and/or other element that may be formed on and extend from exposed surface 126 of rotor 110.

FIG. 2 also depicts an inspection system 130, according to embodiments. Portions of inspection system 130 may be positioned on or adjacent rotor 110 in order to perform an inspection of rotor 110 and/or the plurality of features 128 formed on rotor 110. Inspection system 130 may include at least one transmitter probe 132 (hereafter, "transmitter probe 132") positioned on or substantially adjacent to exposed surface 126 of rotor 110. When positioned on exposed surface 126, transmitter probe 132 may be releasably coupled to rotor 110 during the inspection process discussed herein. Alternatively, when transmitter probe 132 is positioned adjacent exposed surface 126, transmitter probe 132 may be suspended in the space directly adjacent to rotor 110 using any suitable device or system capable of holding and/or positioning transmitter probe 132 adjacent rotor 110. Additionally, as shown in FIG. 2, transmitter probe 132 may be positioned adjacent a first side 134 of the plurality of features 128 (e.g., dovetail) formed on and extending from exposed surface 126 of rotor 110. Transmitter probe 132 may be configured to transmit energy toward and/or through rotor 110. As discussed in detail below, the energy transmitted by transmitter probe 132 may be utilized to inspect rotor 110 and/or the plurality of features 128 formed on rotor 110, and may be used to maintain a desired spacing and/or alignment between transmitter probe 132 and a receiver probe of inspection system 130 during the inspection process. In a non-limiting example, transmitter probe 132 may be an ultrasonic, phased array transducer that may transmit ultrasonic energy. Although one transmitter probe 132 is depicted in FIG. 2, it is understood that a plurality of transmitter probes may be positioned on rotor 110 and utilized in the inspection process discussed herein.

Transmitter probe 132 may be configured to move around rotor 110. Specifically, transmitter probe 132 may be configured to move circumferentially around exposed surface 126 of rotor 110 during the inspection process. In a non-limiting example where transmitter probe 132 is positioned on and/or releasably coupled to rotor 110, transmitter probe 132 may move circumferentially around rotor 110 along exposed surface 126. In another non-limiting example where transmitter probe 132 is positioned adjacent exposed surface 126 of rotor 110, the suitable device or system holding and/or positioning transmitter probe 132 adjacent rotor 110 may move transmitter probe 132 circumferentially around rotor 110 along exposed surface 126.

As shown in FIG. 2, inspection system 130 may include a first propulsion assembly 136 that may automate the movement of transmitter probe 132 around rotor 110 and/or along exposed surface 126. First propulsion assembly 136 may be coupled or fixed to transmitter probe 132, and may contact exposed surface 126 of rotor 110. As a result of contacting exposed surface 126, first propulsion assembly 136 may also releasable couple and/or position transmitter probe 132 on exposed surface 126 of rotor 110 as well. First propulsion assembly 136 may include any suitable elements, device and/or components that may be configured to move transmitter probe 132 along exposed surface 126 of rotor 110. In a non-limiting example, first propulsion assembly 136 may include a plurality of magnetic wheels that may contact, move along and magnetically couple transmitter probe 132 to exposed surface 126 of rotor 110. In the non-limiting example, first propulsion assembly 136 may also include a drivetrain system coupled to and configured to drive the magnetic wheels of first propulsion assembly 136 to move transmitter probe 132 along exposed surface 126 and around rotor 110. Furthermore, first propulsion assembly 136 may include a magnetic track coupled to exposed surface 126 of rotor 110, which may receive the magnetic wheels and maintain transmitter probe 132 on a desired path (e.g., maintain distance (D) between transmitter probe 132 and a receiver probe) when moving around rotor 110. As discussed herein, first propulsion assembly 136 may be in communication with a probe alignment system which may engage first propulsion assembly 136 to move transmitter probe 132 around rotor 110, and adjust displacement characteristics of transmitter probe 132 using first propulsion assembly 136 to maintain an alignment between transmitter probe 132 and at least one receiver probe of inspection system 130.

In another non-limiting example, transmitter probe 132 may be manually moved along exposed surface 126 of rotor 110. Similar to first propulsion assembly 136 shown in FIG. 2, inspection system 130 may include suitable devices, components and/or assemblies for allowing transmitter probe 132 to be manually moved around rotor 110 and/or along exposed surface 126. Similar to the example discussed above, a plurality of magnetic wheels may be coupled to transmitter probe 132 and may contact, move along and magnetically couple transmitter probe 132 to exposed surface 126 of rotor 110. An operator performing the inspection process on rotor 110 may manually move transmitter probe 132 along exposed surface 126 and around rotor 110 as discussed herein. In the non-limiting example where transmitter probe 132 is moved manually, the magnetic wheels on transmitter probe 132 may maintain the releasable coupling between transmitter probe 132 and rotor 110, while allowing the operator to move transmitter probe 132 along exposed surface 126 with minimal friction. In the non-limiting example where transmitter probe 132 is moved manually and as discussed in detail below, first propulsion assembly 136 may be in communication with a probe alignment system which may analyze energy characteristics of inspection system 130 and provide indicators to an operator when displacement characteristics of transmitter probe 132 may require adjustment. Adjusting the displacement characteristics of transmitter probe 132 may maintain an alignment between transmitter probe 132 and at least one receiver probe of inspection system 130 during the inspection process.

As shown in FIG. 2, inspection system 130 may also include at least one receiver probe 138 (hereafter, "receiver probe 138"). Receiver probe 138 may be positioned on or substantially adjacent to exposed surface 126 of rotor 110. Similar to transmitter probe 132, when receiver probe 138 is positioned on exposed surface 126, receiver probe 138 may be releasably coupled to rotor 110. Alternatively, when receiver probe 138 is positioned adjacent exposed surface 126, receiver probe 138 may be suspended in the space direct adjacent to rotor 110 using a similar device or system as transmitter probe 132, as discussed herein. As shown in FIG. 2, receiver probe 138 may be positioned adjacent a second side 140 of the plurality of features 128 (e.g., dovetail) formed on and extending from exposed surface 126 of rotor 110. Specifically, receiver probe 138 may be positioned adjacent a second side 140, opposite the first side 134 of the plurality of features 128 of rotor 110 and/or opposite transmitter probe 132. As shown in FIG. 2, the plurality of features 128 of rotor 110 may substantially separate transmitter probe 132 and receiver probe 138, and may also substantially obstruct, obscure and/or block a line of sight between transmitter probe 132 and receiver probe 138. As a result of separating transmitter probe 132 and receiver probe 138, the plurality of features 128 of rotor 110 may substantially prevent transmitter probe 132 from transmitting energy directly to receiver probe 138, as discussed herein.

Receiver probe 138 may be configured to receive and/or detect energy. Specifically, receiver probe 138 may be configured to receive the energy transmitted from transmitter probe 132 of inspection system 130. In a non-limiting example, transmitter probe 132 and receiver probe 138 may use a "pitch-catch" technique or process for transmitting and receiving energy. As shown in FIG. 2, the energy transmitted by transmitter probe 132 may pass through rotor 110 to a focal point 142 of rotor 110. The energy may deflect and/or bounce from focal point 142 toward receiver probe 138. In another non-limiting example, transmitter probe 132 may focus energy toward focal point 142 and receiver probe 138 may only detect energy transmitted to focal point 142. The focal point 142 may change and/or move as transmitter probe 132 and receiver probe 138 move along and/or around rotor 110, as discussed herein.

The energy transmitted by transmitter probe 132 may be received by receiver probe 138 to inspect rotor 110 and/or the plurality of features 128 formed on rotor 110 and determine if rotor 110 includes defects, and/or requires maintenance before being implemented back into steam turbine steam 100. Additionally, the energy transmitted by transmitter probe 132 may be received by receiver probe 138, and energy characteristics (e.g., amplitude, time of flight and so on) relating to the received energy may be utilized, processed and/or analyzed to maintain a desired spacing and/or alignment between transmitter probe 132 and receiver probe 138 of inspection system 130 during the inspection process. As discussed in detail below, maintaining a desired spacing and/or alignment between transmitter probe 132 and receiver probe 138 may be critical to ensuring that inspection system 130 may adequately inspect rotor 110 and/or the plurality of features 128. In a non-limiting example, transmitter probe 132 may be an ultrasonic, phased array sensor or receiver that may receive and/or detect ultrasonic energy. Although one receiver probe 138 is depicted in FIG. 2, it is understood that a plurality of receiver probes may be positioned on rotor 110 and utilized in the inspection process discussed herein. Additionally, the number of receiver probes 138 of inspection system 130 may directly correlate with, or may be substantially dependent from, the number of transmitter probes 132 of inspection system 130.

Although discussed herein as transmitter probe 132 solely transmitting energy, and receiver probe 138 solely receiving energy, it is understood that the probes of inspection system 130 may perform different tasks and/or functions. In a non-limiting example, each probe (e.g., transmitter probe 132, receiver probe 138) of inspection system 130 may be configured to both transmit and receive energy. That is, a first probe (e.g., transmitter probe 132) positioned adjacent a first side of feature 128 formed on rotor 110 may be configured to transmit energy toward a second probe (e.g., receiver probe 138) and also receive energy transmitted by the second probe. Similarly, the second probe positioned adjacent a second side of feature 128, opposite the first side, may also be configured to transmit energy toward the first probe and receive energy transmitted by the first probe. The functions and/or operations of transmitter probe 132 and receiver probe 138 discussed herein may be limited to performing a single operation (e.g., transmitting energy, receiving energy) merely for simplicity in description of inspection system 130.

Similar to transmitter probe 132, receiver probe 138 may be configured to move around rotor 110. Specifically, receiver probe 138 may be configured to move circumferentially around exposed surface 126 of rotor 110 during the inspection process. As shown in FIG. 2, inspection system 130 may include a second propulsion assembly 144 that may automate the movement of transmitter probe 132 around rotor 110 and/or along exposed surface 126. Second propulsion assembly 144 may be coupled or fixed to receiver probe 138, and may contact exposed surface 126 of rotor 110. As a result of contacting exposed surface 126, second propulsion assembly 144 may releasable couple and/or position receiver probe 138 on exposed surface 126 of rotor 110. Second propulsion assembly 144 may include any suitable elements, device and/or components (e.g., magnetic wheels, drivetrain system and the like) that may be configured to move receiver probe 138 along exposed surface 126 of rotor 110, as similarly discussed herein with respect to first propulsion assembly 136. As discussed herein, and similar to first propulsion assembly 136, second propulsion assembly 144 may be in communication with a probe alignment system which may engage second propulsion assembly 144 to move receiver probe 138 around rotor 110. Additionally, and as discussed herein, the probe alignment system may adjust displacement characteristics of receiver probe 138 using second propulsion assembly 144 to maintain an alignment between transmitter probe 132 and receiver probe 138 during the inspection process.

Inspection system 130 may also include probe alignment system 146. As shown in FIG. 2, probe alignment system 146 may be coupled to, operably connected to and/or in electrical communication with transmitter probe 132 and receiver probe 138 of inspection system 130. As discussed herein, probe alignment system 146 may be in electrical communication with transmitter probe 132 and receiver probe 138 such that probes 132, 138 may provide information, data and/or energy characteristics relating to the energy transmitted by transmitter probe 132 and/or received by receiver probe 138. As discussed herein, probe alignment system 146 may analyze the energy characteristics to determine if displacement characteristics for the transmitter probe 132 and/or receiver probe 138 require adjustment. Additionally as discussed herein, probe alignment system 146 may also be operably connected to and/or in electrical communication with first propulsion assembly 136 and second propulsion assembly 144 to adjust displace characteristics of transmitter probe 132 and/or receive probe 138 using propulsion assemblies 136, 144. In non-limiting examples, the energy characteristics may include an amplitude of the energy received by receiver probe 138, a time of flight or travel for the energy to be transmitted from transmitter probe 132 and received by receiver probe 138, and any other energy-related information that may be detected by receiver probe 138, analyzed by probe alignment system 146 and utilized to maintain a desired alignment or spacing between transmitter probe 132 and receiver probe 138 during an inspection process, as discussed herein.

As shown in FIG. 2, probe alignment system 146 may include an energy module 148, a probe displacement module 150 and a storage device 152. Energy module 148, probe displacement module 150 and storage device 152 may all be operably connected and/or in electrical communication with one another. As a result, energy module 148, probe displacement module 150 and storage device 152 may share, obtain and/or transfer data during the inspection process. Energy module 148 may be configured to obtain the energy characteristics relating to the energy received by receiver probe 138 and analyze the energy characteristics to determine if displacement characteristics of transmitter probe 132 and/or receiver probe 138 require adjustment.

Probe displacement module 150 may be configured to receive information from energy module 148 when energy module 148 determines that displacement characteristics of transmitter probe 132 and/or receiver probe 138 require adjustment. Additionally, probe displacement module 150 may be configured to perform additional processes to ensure transmitter probe 132 and receiver probe 138 remain and/or are moved back into a desired alignment and/or spacing when performing the inspection process. In a non-limiting example where the movement of transmitter probe 132 and receiver probe 138 is automated (e.g., propulsion assemblies), probe displacement module 150 may also be configured to adjust the displacement characteristics of transmitter probe 132 and/or receiver probe 138 based on the analyzed energy characteristics and determination of energy module 148. In another non-limiting example where the movement of transmitter probe 132 and receiver probe 138 is manually performed (e.g., operator), probe displacement module 150 may be configured to provide instructions to the operator regarding the specific displacement characteristics for transmitter probe and/or receiver probe 138 that require adjustment. Probe displacement module 150 may provide instructions to the operator via an output device (e.g., computer display, printer and so on) (not shown) in communication with probe alignment system 146. The displacement characteristics for transmitter probe 132 and receiver probe 138 may include, but are not limited to, the speed in which probes 132, 138 move along exposed surface 126 and/or around rotor 110, a circumferential position of probes 132, 138 with respect to rotor 110, an axial position of probes 132, 138 with respect to rotor 110, an axial distance (D) between probes 132, 138 and other characteristics that maintain a desired alignment or spacing between transmitter probe 132 and receiver probe 138 during an inspection process, as discussed herein.

Storage device 152 may be configured to store information and/or data relating to the inspection process performed by the inspection system 130, and more specifically, information and/or data pertaining to the alignment and/or spacing between transmitter probe 132 and receiver probe 138 when performing the inspection process. The information may be stored on storage device 152 prior to performing the inspection process. In a non-limiting example, a predetermined desired amplitude and/or a predetermined desired time of flight for the energy transmitted by transmitter probe 132 may be stored on storage device 152 and sent or obtained by energy module 148 when analyzing the energy characteristics, as discussed herein. Additionally, the information stored on storage device 152 may be provided and/or continuously updated while performing the inspection process. For example, energy module 148 may receive energy characteristics for the energy received by receiver probe 138 and may be configured to determine a desired amplitude and/or desired time of flight or the energy based on the energy characteristics. Once energy module 148 determines the desired amplitude and/or desired time of flight, energy module 148 may provide and store that information and/or data to storage device 152. During the analyze of energy characteristics, energy module 148 may obtain and/or recall the stored information and/or data (e.g., desired amplitude) from storage device 152, and compare the stored information and/or data from storage device 152 with the energy characteristics (e.g., detected amplitude) for the energy received by receiver probe 138.

Although shown as a standalone component and/or system, it is understood that probe alignment system 146 may be formed integrally with and/or may be a portion of an overall system or component used when inspecting rotor 110. That is, probe alignment system 146 may be its own system, or alternatively, may be part of a larger system that is in communication with transmitter probe 132 and receiver probe 138, and is utilized to perform the inspection process discussed herein.

Aligning and maintaining an alignment for transmitter probe 132 and receiver probe 138 while performing an inspection process on rotor 110 may now be discussed with reference to FIG. 2. During the inspection process transmitter probe 132 and receiver probe 138 may be coupled to and/or positioned on exposed surface 126 of rotor 110. Transmitter probe 132 may transmit ultrasonic energy through and/or around rotor 110 and receiver probe 138 may receive the ultrasonic energy in order to detect defects of rotor 110 and/or determine the need for maintenance before utilizing rotor 110 in steam turbine system 100 (see, FIG. 1). In order to inspect the entire rotor 110, transmitter probe 132 and receiver probe 138 may utilize propulsion assemblies 136, 144 to move transmitter probe 132 and receiver probe 138 circumferentially around rotor 110.

In order to obtain the most accurate inspection information about rotor 110 using inspection system 130, transmitter probe 132 and receiver probe 138 should maintain an optimum positioning on rotor 110, axial spacing and/or axial alignment when performing the inspection process. The optimum positioning, spacing and/or alignment may be based on and/or determined using energy characteristics for the ultrasonic energy received by receiver probe 138 of inspection system 130. Specifically, energy module 148 of probe alignment system 146 may determine a desired amplitude and/or desired time of flight for the energy received by receiver probe 138 that may ensure that transmitter probe 132 and receiver probe 138 are performing the most accurate inspection of rotor 110 during the inspection process. In a non-limiting example, the desired amplitude may be a maximum amplitude for the energy transmitted by transmitter probe 132 and received by receiver probe 138. Additionally, the desired time of flight for the energy received by receiver probe 138 may be 0.25 seconds. The amplitude and/or time of flight for the energy received by receiver probe 138 may be dependent, at least in part on, the strength and/or operational characteristics of transmitter probe 132, the size (e.g., diameter, circumference) of rotor 110, the material of rotor 110, the size and/or geometry of the plurality of features 128 of rotor 110, and so on.

Once the desired amplitude and/or desired time of flight for the energy is determined, probe alignment system 146 may continuously, or periodically, obtain/receive, and subsequently analyze energy characteristics from receiver probe 138 during the inspection process. The energy characteristics may include the actual or detected amplitude and/or time of flight for the energy being received by the receiver probe 138 while inspection system 130 is performing the inspection process on rotor 110. In analyzing the energy characteristics, energy module 148 of probe alignment system 146 may compare the detected amplitude and/or time of flight for the energy received by the receiver probe 138 with the desired amplitude and/or time of flight to determine if the detected amplitude and/or time of flight differ from the desired amplitude and/or time of flight. If the detected amplitude and/or time of flight do not differ from the desired amplitude and/or time of flight, probe alignment system 146 may determine that transmitter probe 132 and receiver probe 138 are optimally positioned, spaced and/or aligned to provide the most accurate inspection of rotor 110. As such, the displacement characteristics of transmitter probe 132 and/or receiver probe 138 may not require adjustment. However, if the detected amplitude and/or time of flight do differ from the desired amplitude and/or time of flight, energy module of probe alignment system 146 may determine that the displacement characteristics of transmitter probe 132 and/or receiver probe 138 may require adjustment so transmitter probe 132 and receiver probe 138 may subsequently provide the most accurate inspection of rotor 110.

When energy module 148 of probe alignment system 146 determines that displacement characteristics of transmitter probe 132 and/or receiver probe 138 may require adjustment, energy module 148 may communicate with probe displacement module 150. Specifically, energy module 148 may identify and/or instruct probe displacement module 150 that displacement characteristics of transmitter probe 132 and/or receiver probe 138 may require adjustment, and may also provide information relating to the energy characteristics for the energy received by receiver probe 138. The information relating to the energy characteristics provided to probe displacement module 150 may include how the detected amplitude and/or time of flight differs from the desired amplitude and/or time of flight (e.g., greater than, less than). Probe displacement module 150 may utilize and/or analyze the information relating to the energy characteristics provided by energy module 148 to determine which displacement characteristic(s) of transmitter probe 132 and/or receiver probe 138 may be adjusted to put transmitter probe 132 and receiver probe 138 back in an optimally position, spacing and/or alignment for the inspection process.

In a non-limiting example, energy module 148 may determine that the detected amplitude does not differ from the desired amplitude, but the detected time of flight is less than the desired time of flight. In this non-limiting example, probe displacement module 150 may determine that the receiver probe 138 is staggered to far behind the transmitter probe 132, and needs to be moved forward. As a result, the speed of transmitter probe 132 may be temporarily decreased and/or the speed of receiver prove 138 may be temporarily increased until it is determined that the detected time of flight does not differ (e.g., equal) from the desired time of flight.

Figure 3:
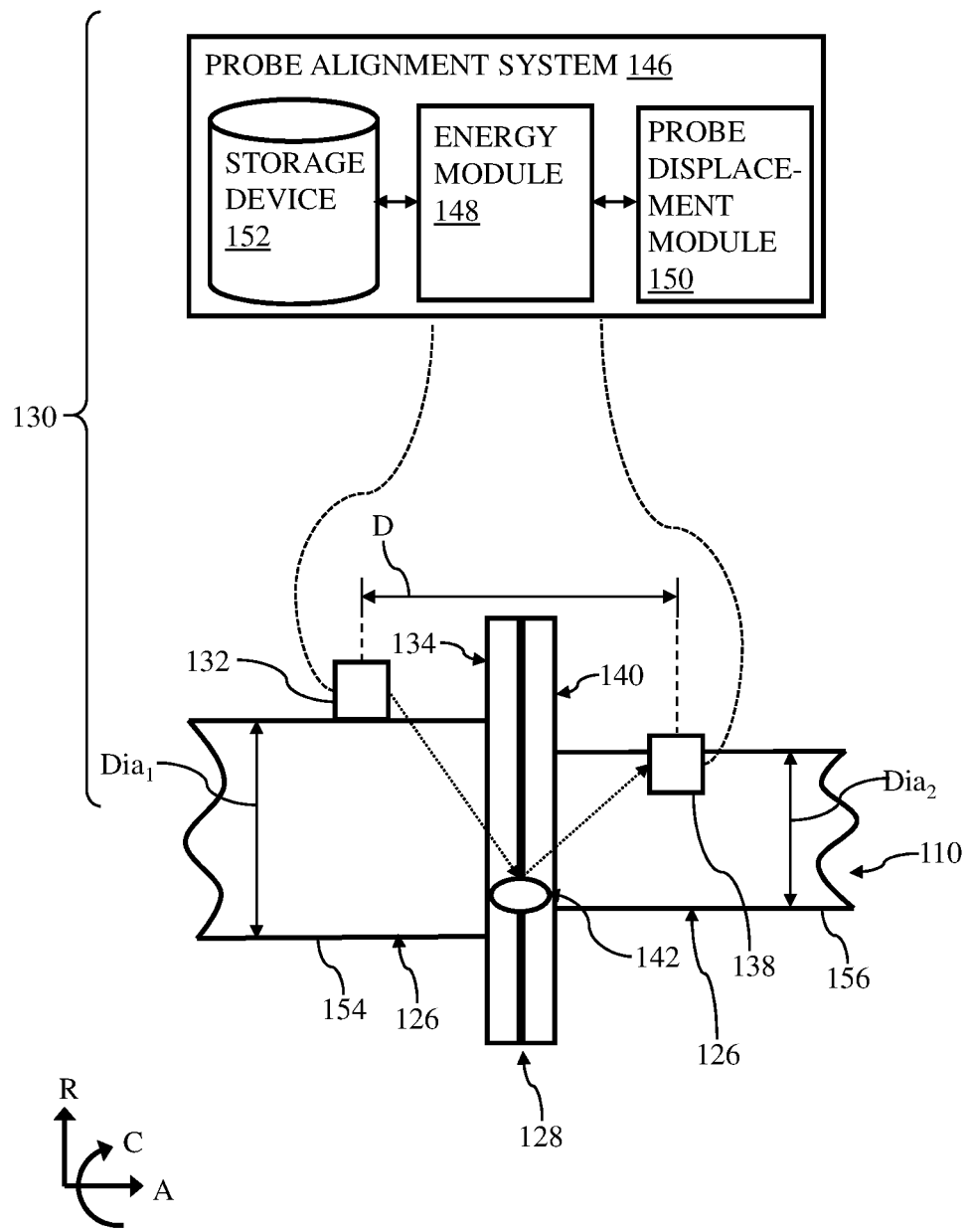
FIG. 3 depicts a side view of a distinct portion of a rotor of the steam turbine system of FIG. 1, and an inspection system, according to embodiments.

In another non-limiting example, energy module 148 may determine that the detected amplitude differs from or is less than the desired amplitude, but the detected time of flight does not differ from the desired time of flight. In this non-limiting example, probe displacement module 150 may determine that transmitter probe 132 and receiver probe 138 is axially separated beyond an optimum or desired distance (D), and the axial position of transmitter probe 132 and/or receiver probe 138 needs to be adjusted. In the non-limiting example, receiver probe 138 may be moved axially toward transmitter prove 132 and feature 128 until transmitter probe 132 and receiver probe 138 are axially spaced or separated by an optimum or desired distance (D), as shown in FIG. 3. Once transmitter probe 132 and receiver probe 138 are axially spaced or separated by the desired distance (D), the detected amplitude may not differ (e.g., equal) from the desired amplitude.

In another non-limiting example, energy module 148 may determine that the detected amplitude differs from or is less than the desired amplitude, but the detected time of flight does not differ from the desired time of flight. In this non-limiting example, probe displacement module 150 may determine that transmitter probe 132 and receiver probe 138 is axially separated beyond an optimum or desired distance (D), and the axial position of transmitter probe 132 and/or receiver probe 138 needs to be adjusted. In the non-limiting example, receiver probe 138 may be moved axially toward transmitter prove 132 and feature 128 until transmitter probe 132 and receiver probe 138 are axially spaced or separated by an optimum or desired distance (D), as shown in FIG. 3. Once transmitter probe 132 and receiver probe 138 are axially spaced or separated by the desired distance (D), the detected amplitude may not differ (e.g., equal) from the desired amplitude.

In a further non-limiting example, energy module 148 may determine that the detected amplitude and time of flight differ from the desired amplitude and time of flight. In this non-limiting example, probe displacement module 150 may adjust one or more displacement characteristics (e.g., speed, position, axial separation and so on) for transmitter probe 132 and/or receiver probe 138 until the detected amplitude and time of flight no longer differ from the desired amplitude and time of flight.

As discussed herein, probe displacement module 150 may adjust the displacement characteristics for transmitter probe 132 and/or receiver probe 138 by providing instructions and/or electrical signals to the respective propulsion assemblies 136, 144 coupled to and configured to move transmitter probe 132 and/or receiver probe 138. In another non-limiting example where transmitter probe 132 and receiver probe 138 are manually moved around rotor 110 during the inspection process, probe displacement module 150 may provide instructions to the operator of inspection system 130 highlighting and/or indicating the adjustments that need to be made to transmitter probe 132 and/or receiver probe 138.

As shown in FIG. 2, transmitter probe 132 and receiver probe 138 may be in axial alignment and/or in a similar axial plane when in an optimal position, spacing and/or alignment to provide the most accurate inspection of rotor 110. This may be a result of rotor 110 having a uniform and/or single diameter and/or circumference. That is, the portion of rotor 110 that transmitter probe 132 is position on may have the same diameter and circumference as the portion of rotor 110 that receiver probe 138 is positioned on. As a result, when transmitter probe 132 and receiver probe 138 are optimally positioned, spaced and/or aligned, the probes 132, 138 may also be in axial alignment with respect to rotor 110. Although shown as aligned, it is understood that the positioning and/or spacing of transmitter probe 132 and receiver probe 138 shown in FIG. 2 is merely exemplary, and is not limiting. As discussed herein, the optimal positioning, spacing and/or alignment is dependent on a desired amplitude and time of flight for the energy received by receiver probe 138. As such, transmitter probe 132 and receiver probe 138 may be axially staggered on rotor 110 and still optimally positioned, spaced and/or alignment, regardless of the configuration and/or geometry (e.g., diameter, circumference) of rotor 110 undergoing the inspection process discussed herein.

FIG. 3 depicts a side view of a distinct portion of rotor 110 of steam turbine system 100, according to embodiments. FIG. 3 also depicts inspection system 130 used to inspect the distinct portion of rotor 110, as discussed herein. Propulsion assemblies 136, 142 have been omitted from FIG. 3 for clarity. However, it is understood that transmitter probe 132 and/or receiver probe 138 may include propulsion assemblies 136, 142, respectively, for moving the probes along exposed surface 126 of rotor 110, as discussed herein with respect to FIG. 2. It is understood that similarly numbered and/or named components may function in a substantially similar fashion. Redundant explanation of these components has been omitted for clarity.

The distinct portion of rotor 110 depicted in FIG. 3 may include two distinct segments. Specifically, and as shown in FIG. 3, the depicted portion of rotor 110 may include a first segment 154 and a second segment 156 coupled to first segment 154. First segment 154 and second segment 156 may be coupled using any suitable coupling and/or material joining technique including, but not limited to, welding, brazing, mechanical fastening, and the like. As discussed herein, rotor 110 may include a plurality of features 128. In the non-limiting example shown in FIG. 3, the coupling joint formed between first segment 154 and second segment 156 may be a feature 128 of rotor 110. As discussed herein, the feature 128 (e.g., joint) of rotor 110 may substantially obstruct, obscure and/or block a line of sight between transmitter probe 132 and receiver probe 138.

As shown in FIG. 3, first segment 154 and second segment 156 may have varying diameters. More specifically, first segment 154 may include a first diameter ($Dia_1$) and second segment 156 may include a second diameter ($Dia_2$), distinct from the first diameter ($Dia_1$) of first segment 154. In the non-limiting example shown in FIG. 3, the first diameter ($Dia_1$) of first segment 154 may be larger than the second diameter ($Dia_2$) of second segment 156. As a result, a circumference for first segment 154 may also be larger than a circumference for second segment 156.

As a result of the varying diameters and/or circumferences for first segment 154 and second segment 156 forming rotor 110, transmitter probe 132 and receiver probe 138 may not be aligned in similar positions and/or in a similar manner as when rotor 110 has a uniform or single diameter (see, FIG. 2). In the non-limiting example shown in FIG. 3, transmitter probe 132 and receiver probe 138 of inspection system 130 may be positioned such that the amplitude and time of flight for the energy received by receiver probe 138 is equal to the desired amplitude and/or time of flight for optimum inspection of rotor 110, as discussed herein. Compared to the example in FIG. 2, transmitter probe 132 and receiver probe 138 may be axially out of alignment. That is, transmitter probe 132 positioned on first segment 154 may be axially staggered from and/or in a distinct axial plane than receiver probe 138 positioned on second segment 156. The staggering between transmitter probe 132 and receiver probe 138 to maintain the desired amplitude and/or time of flight for the energy received by receiver probe 138 may be a result of the distinct diameters between first segment 154 and second segment 156. Although transmitter probe 132 is shown as being staggered and/or positioned in front of receiver probe 138 it is understood that this is merely a non-limiting example, and in some instances, receiver probe 138 may be positioned in front of transmitter probe 132 during an inspection process.

Figure 4:
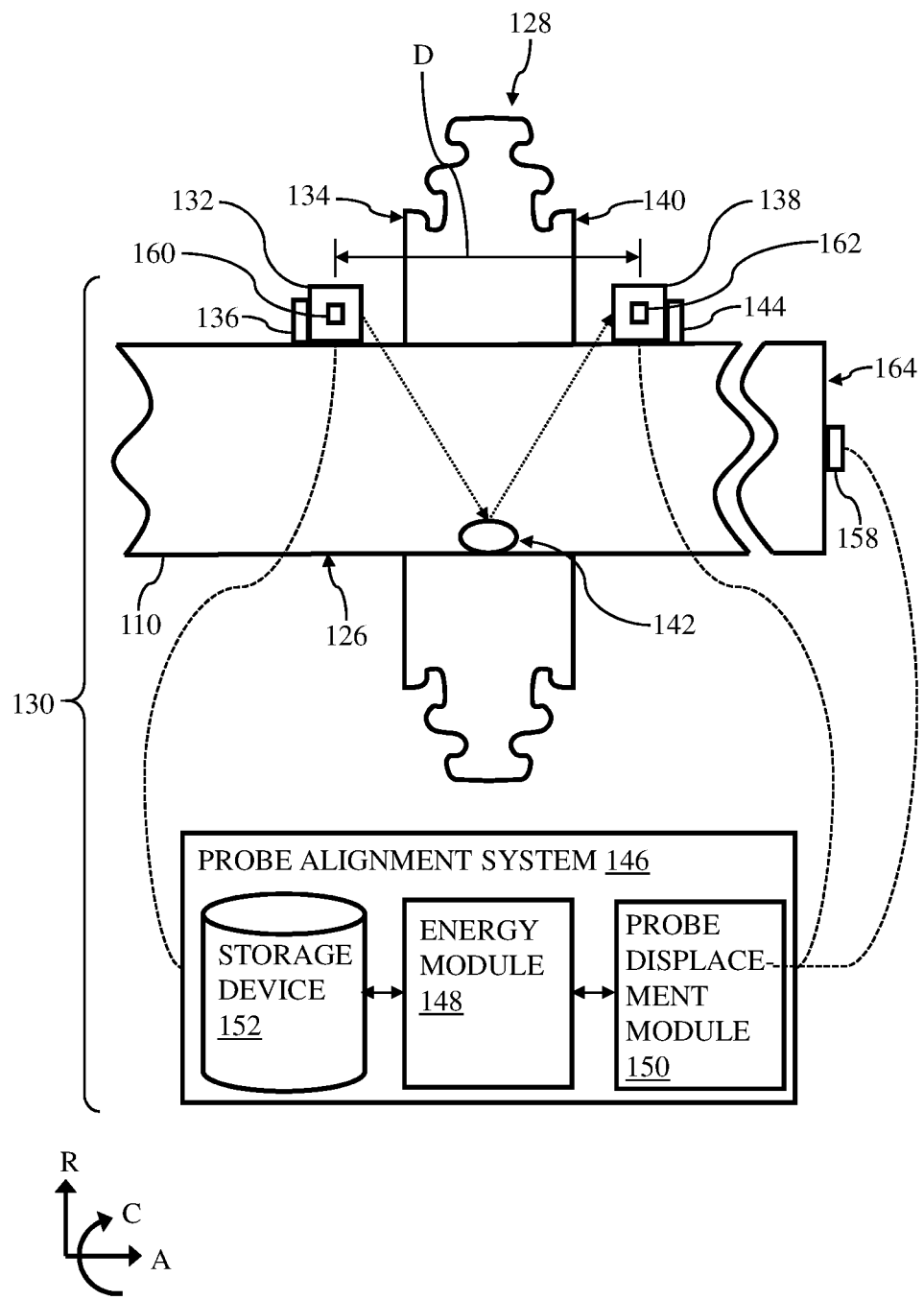
FIG. 4 depicts a side view of a portion of a rotor of the steam turbine system of FIG. 1, and an inspection system, according to additional embodiments.

FIG. 4 depicts a side view of a portion of rotor 110 of steam turbine system 100 similar to the portion shown in FIG. 2. FIG. 4 also depicts inspection system 130 used to inspect the distinct portion of rotor 110, as discussed herein. It is understood that similarly numbered and/or named components may function in a substantially similar fashion. Redundant explanation of these components has been omitted for clarity.

Inspection system 130 shown in FIG. 4 may include additional components used to align and/or maintain alignment between transmitter probe 132 and receiver probe 138 during the inspection process of rotor 110 discussed herein. Specifically, inspection system 130 may also include an encoder 158 and inclinometers 160, 162. As shown in FIG. 4, encoder 158 may be positioned on an end 164 of rotor 110 of steam turbine system 100. Specifically, encoder 158 may be coupled to end 164 of rotor 110 and may be positioned in axial alignment with a center of rotor 110. Encoder 158 may be operably connected to and/or in electrical communication with probe alignment system 146 and inclinometers 160, 162 of inspection system 130. In a non-limiting example, encoder 158 may be hardwired to probe alignment system 146 and may in wireless communication with inclinometers 160, 162 in order to share data from inclinometers 160, 162 with probe alignment system 146. As discussed herein, encoder 158 may define a "0 degree" mark or reference for inclinometers 160, 162 coupled to transmitter probe 132 and receiver probe 138, respectively, so probe alignment system 146 may detect the circumferential movement and/or position of transmitter probe 132 and receiver probe 138 as they move around rotor 110.

As shown in FIG. 4, first inclinometer 160 may be coupled to, formed and/or positioned on transmitter probe 132, and a second inclinometer 162 may be coupled to, formed and/or positioned on receiver probe 138. In another non-limiting example, first inclinometer 160 may be coupled to and/or positioned on first propulsion assembly 136, and second inclinometer 162 may be coupled to and/or positioned on second propulsion assembly 144. Inclinometers 160, 162 may also move with the respective probes 132, 138 during the inspection process. Specifically, first inclinometer 160 coupled to and/or positioned on transmitter probe 132 may move with and/or be carried by transmitter probe 132 as transmitter probe 132 moves along exposed surface 126 of rotor 110 during the inspection process. Additionally, second inclinometer 162 coupled to and/or positioned on receiver probe 138 may move with and/or be carried by receiver probe 138 as receiver probe 138 moves along exposed surface 126 of rotor 110 during the inspection process. In a non-limiting example, inclinometers 160, 162 may be operably connected to and/or in electrical communication with probe alignment system 146 for transmitting data or information relating to the position (e.g., angle) of transmitter probe 132 and receiver probe 138, respectively, to probe alignment system 146 during the inspection process. Inclinometers 160, 162 may be any suitable instruments or components that may be configured to detect and/or measure the angle of transmitter probe 132 and receiver probe 138 with respect to rotor 110, as discussed herein.

Encoder 158, and inclinometers 160, 162 of inspection system 130 may be utilized to detect and/or determine the circumferential position of transmitter probe 132 and receiver probe 138 on rotor 110 and subsequently aid in the alignment of transmitter probe 132 and receiver probe 138. That is, during the inspection process, encoder 158 positioned on end 164 may define a "0 degree" mark or reference for the circumference of rotor 110 to be utilized by inclinometers 160, 162. Inclinometers 160, 162 may be configured to measure the angle of transmitter probe 132 and receiver probe 138, as defined by encoder 158 (e.g., 0 degree mark), as transmitter probe 132 and receiver probe 138 move around rotor 110 during the inspection process. Specifically, first inclinometer 160 may be configured to measure the angle of transmitter probe 132 and second inclinometer 162 may be configured to measure the angle of receiver probe 138 during the inspection process. Data or information relating to the angle of transmitter probe 132 and receiver probe 138 may be sent and/or transmitted to encoder 158 and/or probe alignment system 146 to be analyzed by probe alignment system 146. As similarly discussed above with respect to analyzing the energy characteristics transmitted by receiver probe 138, the data or information relating to the angle of transmitter probe 132 and receiver probe 138 obtained by encoder 158 and/or inclinometers 160, 162 may be utilized to ensure transmitter probe 132 and receiver probe 138 remain and/or are moved back into a desired (axial) alignment when performing the inspection process. In a non-limiting example, first inclinometer 160 may determine that transmitter probe 132 is positioned at the 180° mark on rotor 110, and second inclinometer 160 may determine that receiver probe 138 is positioned at the 145° mark on rotor 110. In the non-limiting example, it may be determined that transmitter probe 132 and receiver probe 138 should be in axial alignment on rotor 110 to ensure the most accurate inspection results. As a result, probe alignment system 146 may determine that transmitter probe 132 and receiver probe 138 are not properly aligned based on the data from inclinometers 160, 162 and may subsequently adjust the displacement characteristics (e.g., speed, position) of transmitter probe 132 and/or receiver probe 138 to put the probes 132, 138 in axial alignment (e.g., 180° mark).

In a non-limiting example, encoder 158 and inclinometers 160, 162 may be concurrently or simultaneously with transmitter probe 132 and receiver probe 138 for detecting and/or maintaining alignment of transmitter probe 132 and receiver probe 138 during the inspection process. In another non-limiting example, encoder 158 and inclinometers 160, 162 may be used exclusively for detecting and/or the circumferential position of transmitter probe 132 and receiver probe 138 to ensure alignment between transmitter probe 132 and receiver probe 138 during the inspection process. In this non-limiting example, transmitter probe 132 and receiver probe 138 may still perform operations discussed herein to ensure a desired spacing or distance (D) is maintained between transmitter probe 132 and receiver probe 138 during the inspection process.

Figure 5:
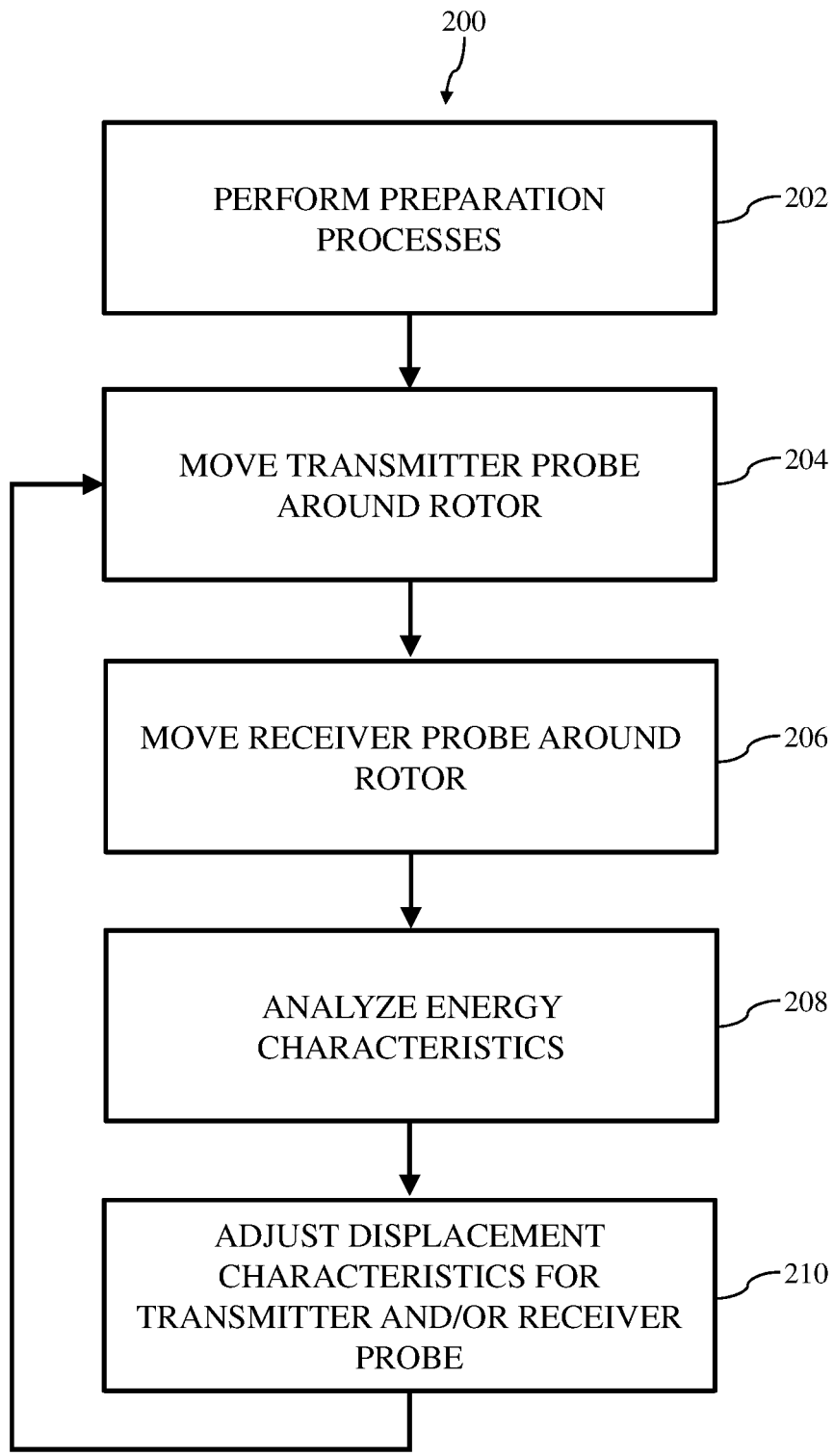
FIG. 5 depicts a flow chart of a process for aligning inspection probes of an inspection system, according to embodiments.

FIG. 5 depicts an example process for aligning inspection probes of an inspection system. Specifically, FIG. 5 is a flowchart depicting one example process 200 for aligning and maintaining alignment between a transmitter probe and a receiver probe of an inspection system while performing an inspection process on a rotor.

In operation 202, initial preparation processes may be performed. Specifically, preparation processes may be performed on the rotor that may undergo the inspection process using the inspection system. The preparation processes may include, but are not limited to, removing the rotor from a housing and/or enclosure of the turbine system, and roughening the surface of the rotor. Roughening the surface of the rotor may include, for example, sand-blasting the surface of the rotor to improve inspection results. Preparation processes can also include releasably coupling at least one transmitter probe and at least one receiver probe to the exposed surface of the rotor. The transmitter probe may be releasably coupled to the rotor on a first side of a feature of the rotor, and the receiver probe may be releasably coupled to the rotor on a second side of the feature. The second side of the feature may be opposite the first side. As such, the feature may substantially block the line of sight between the transmitter probe and the receiver probe.

In operation 204, the transmitter probe releasably coupled to the rotor may be moved on the rotor. Specifically, the transmitter probe may be moved along the exposed surface of the rotor and/or may move circumferentially around the exposed surface of the rotor. In a non-limiting example, the movement of the transmitter probe may automated and the transmitter probe may include a propulsion assembly configured to move the transmitter probe around the rotor. In another non-limiting example, the movement of the transmitter probe may be done manually by an operator performing the inspection process on the rotor.

In operation 206, the receiver probe releasably coupled to the rotor may also be moved around the rotor. Specifically, and similar to the movement of the transmitter probe in operation 204, the receiver probe may be moved along the exposed surface of the rotor and/or may move circumferentially around the exposed surface of the rotor. In non-limiting examples, the movement of the receiver probe may automated (e.g., a propulsion assembly), or alternatively, may be manual (e.g., operator).

Although shown in FIG. 5 as being linear and/or performed in succession, it is understood that operation 204 and operation 206 may be performed simultaneously. That is, the movement of the transmitter probe in operation 204 and the movement of the receiver probe in operation 206 may happen simultaneously, such that both the transmitter probe and receiver probe are both moving along the exposed surface of the rotor. Additionally, it is understood that operation 204 and operation 206 may be performed independent of one another. That is, the movement of the transmitter probe may be independent from the movement of the receiver probe.

In operation 208, energy characteristics for the energy received by the receiver probe may be analyzed. Specifically, energy characteristics including, but not limited to, a detected amplitude and/or a detected time of flight or travel for the energy received by the receiver probe may be analyzed. Analyzing the energy characteristics may also include determining a desired amplitude for the energy received by the receiver probe, and/or determining a desired time of flight for the energy received by the receiver probe. Determining the desired amplitude and/or time of flight may be accomplished when performing the analysis process in operation 208. Alternatively, determining the desired amplitude and/or time of flight may be accomplished prior to the analysis process in operation 208. For example, the desired amplitude and/or time of flight may be determined when performing the initial preparation processes in operation 202. Analyzing the energy characteristics may also include comparing the detected amplitude of the energy received by the receiver probe with the determined, desired amplitude, and determining if the detected amplitude differs from the desired amplitude. Also, analyzing the energy characteristics may include comparing the detected time of flight of the energy received by the receiver probe with the determined, desired time of flight, and determining if the detected time of flight differs from the desired time of flight. If it is determined that the detected amplitude and/or time of flight differs from the determined, desired amplitude and/or time of flight, then the analyzing of operation 208 may also include determining that the transmitter probe and the receiver probe are out of alignment and displacement characteristics of the transmitter probe and/or the receiver probe may require adjustment.

In operation 210, displacement characteristics for the transmitter probe and/or the receiver probe may be adjusted based on the analyzed energy characteristics. Specifically, when it is determined that detected amplitude and/or time of flight differs from the determined, desired amplitude and/or time of flight, displacement characteristics for the transmitter probe and/or the receiver probe may be adjusted to realign and/or reposition the transmitter probe and the receiver probe on the rotor. The realignment and/or repositioning achieved by adjusting displacement characteristics of the transmitter probe and/or the receiver probe may allow the transmitter probe and the receiver probe to provide optimum inspection results when performing the inspection process on the rotor. Adjusting the displacement characteristics of the transmitter probe and/or the receiver probe may include altering a speed of the transmitter probe and/or the receiver probe, altering a circumferential position of the transmitter probe and/or the receiver probe with respect to the rotor, altering an axial position of the transmitter probe and/or the receiver probe with respect to the rotor, and/or altering an axial distance the transmitter probe and/or the receiver probe. Additionally, adjusting the displacement characteristics of the transmitter probe and/or the receiver probe may include axially aligning the transmitter probe and the receiver probe in response to the rotor undergoing the inspection process having a uniform and/or single diameter and circumference. Furthermore, adjusting the displacement characteristics of the transmitter probe and/or the receiver probe may include axially staggering the transmitter probe and the receiver probe in response to the transmitter probe being positioned on a first segment of the rotor having a first diameter and first circumference, and the receiver probe being positioned on a second segment of the rotor having a second diameter and second circumference. The second diameter and second circumference of the second segment may be smaller than the first diameter and first circumference of the first segment.

Although discussed herein as performing an inspection process on a rotor of a turbine, it is understood that the inspection process performed using the inspection system may be performed on any substantially round, and/or circular shaft or component. That is, the inspection process including methods or operations for maintaining an aligning between the inspection probes of the inspection system discussed herein may not be limited to just being performed on a turbine rotor. Rather, the inspection system and alignment operations may be performed on any component that may require inspection and/or may include features that substantially obstruct the line of sight between two inspection probes of the system.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

I claim:

1. An inspection system for inspecting a turbine rotor, the inspection system comprising:
   a first probe for positioning on a circumferential surface of the turbine rotor;
   a first inclinometer for positioning at one of: on the first probe or adjacent the first probe;
   a second probe for positioning on the circumferential surface of the turbine rotor, axially adjacent the first probe;
   a second inclinometer for positioning at one of: on the second probe or adjacent the second probe; and
   a probe alignment system in communication with the first inclinometer and the second inclinometer, the probe alignment system configured to axially align the first probe and second probe on the turbine rotor by:
      adjusting at least one of a first circumferential position of the first probe or a second circumferential position of the second probe in response to determining the first circumferential position of the first probe detected by the first inclinometer is distinct from the second circumferential position of the second probe detected by the second inclinometer.

2. The inspection system of claim 1 further comprising:
   a first propulsion assembly coupled to the first probe, the first propulsion assembly moving the first probe on the circumferential surface of the turbine rotor; and
   a second propulsion assembly coupled to the second probe, the second propulsion assembly moving the second probe on the circumferential surface of the turbine rotor.

3. The inspection system of claim 2, wherein the probe alignment system is in communication with the first propulsion assembly and the second propulsion assembly, and is configured to adjust at least one of the first circumferential position of the first probe or the second circumferential position of the second probe by:
   engaging at least one of: the first propulsion assembly, or the second propulsion assembly until the first circumferential position of the first probe is identical to the second circumferential position of the second probe.

4. The inspection system of claim 2, wherein the probe alignment system is in communication with the first propulsion assembly and the second propulsion assembly, and is configured to adjust at least one of the first circumferential position of the first probe or the second circumferential position of the second probe by:
   adjusting a speed of the at least one of: the first propulsion assembly, or the second propulsion assembly until the first circumferential position of the first probe is identical to the second circumferential position of the second probe.

5. The inspection system of claim 2, wherein the first inclinometer is positioned directly on the first propulsion assembly, adjacent the first probe, and
   the second inclinometer is positioned directly on the second propulsion assembly, adjacent the second probe.

6. The inspection system of claim 1, further comprising:
   an encoder positioned on one of two ends of the turbine rotor formed axially opposite the circumferential surface, the encoder in communication with the first inclinometer and the second inclinometer,
   wherein the encoder defines a zero degree reference mark for the circumferential surface of the turbine rotor.

7. The inspection system of claim 6, wherein probe position data detected by the first inclinometer is based on the zero degree reference mark defined by the encoder, and
   the probe position data detected by the second inclinometer is based on the zero degree reference mark defined by the encoder.

8. The inspection system of claim 7, wherein the first circumferential position of the first probe includes a first circumferential degree determined by a circumferential deviation of the first probe from the zero degree reference mark defined by the encoder, and
   the second circumferential position of the second probe includes a second circumferential degree determined by a circumferential deviation of the second probe from the zero degree reference mark defined by the encoder.

9. The inspection system of claim 8, wherein the probe alignment system is configured to adjust at least one of the first circumferential position of the first probe or the second circumferential position of the second probe by:
   changing at least one of the first circumferential position of the first probe or the second circumferential position of the second probe until the first circumferential degree of the first probe is identical to the second circumferential degree of the second probe.

10. The inspection system of claim 6, wherein the encoder is radially aligned with a center of the end of the turbine rotor.

11. The inspection system of claim 1, wherein the first inclinometer and the second inclinometer are positioned on opposite sides of a feature formed on the circumferential surface of the turbine rotor.

12. The inspection system of claim 1, wherein the probe alignment system is configured to adjust at least one of the first circumferential position of the first probe or the second circumferential position of the second probe by:
   manually moving at least one the first probe or the second probe until the first circumferential position of the first probe is identical to the second circumferential position of the second probe.

13. The inspection system of claim 1, wherein the first circumferential position of the first probe is identified in probe position data detected by the first inclinometer,
   and the second circumferential position of the second probe identified in probe position data detected by the second inclinometer.

* * * * *